United States Patent [19]
Gouge et al.

[11] Patent Number: 5,224,601
[45] Date of Patent: Jul. 6, 1993

[54] WATER SOLUBLE PACKAGE

[75] Inventors: Samuel T. Gouge; James E. Shue, both of Raleigh, N.C.; David B. Edwards; William J. McCarthy, both of Ongar, England

[73] Assignee: Rhone-Poulenc AG Company, Research Triangle Park, N.C.

[21] Appl. No.: 965,526

[22] Filed: Oct. 23, 1992

Related U.S. Application Data

[63] Continuation of Ser. No. 782,092, Oct. 24, 1991, abandoned, which is a continuation-in-part of Ser. No. 713,684, Jun. 11, 1991, abandoned, which is a continuation-in-part of Ser. No. 680,301, Apr. 4, 1991, which is a continuation-in-part of Ser. No. 679,290, Apr. 2, 1991, abandoned, which is a continuation-in-part of Ser. No. 554,615, Jul. 18, 1990, Pat. No. 5,080,226.

[51] Int. Cl.$^5$ ............................................. B65D 85/82
[52] U.S. Cl. .......................... 206/524.7; 71/DIG. 1; 252/315.1; 424/409; 504/116; 504/310; 504/141; 504/318; 504/144
[58] Field of Search ............ 71/DIG. 1, 80, 105; 206/0.5, 204, 205, 219, 484, 524.1, 524.6, 524.7, 525, 568; 252/315.1; 424/409, 412, 405, 406; 514/801, 812

[56] References Cited

U.S. PATENT DOCUMENTS

| | | | |
|---|---|---|---|
| 2,087,368 | 7/1937 | Wilson et al. | 167/35 |
| 2,560,649 | 7/1951 | Hornaday | 15/208 |
| 2,982,394 | 5/1961 | Novak | 206/46 |
| 3,086,007 | 4/1963 | Touey et al. | 260/215 |
| 3,390,507 | 7/1968 | Repko | 53/14 |
| 3,528,921 | 9/1970 | Gray | 252/99 |
| 3,534,851 | 10/1970 | Peterson | 206/0.5 |
| 3,634,260 | 1/1972 | Pickin | 252/95 |
| 3,695,989 | 10/1972 | Albert | 161/160 |
| 3,892,905 | 7/1975 | Albert | 428/220 |
| 4,411,358 | 10/1983 | Bennwik et al. | 206/45.34 |
| 4,416,791 | 11/1983 | Haq | 252/90 |
| 4,540,089 | 9/1985 | Maloney | 206/219 |
| 4,626,372 | 12/1986 | Kaufmann et al. | 252/90 |
| 4,657,134 | 4/1987 | Woodworth et al. | 206/219 |
| 4,681,228 | 7/1987 | Kerry et al. | 206/484 |
| 4,846,992 | 7/1989 | Fonsny | 252/90 |
| 4,885,105 | 12/1989 | Yang et al. | 252/90 |

FOREIGN PATENT DOCUMENTS

| | | |
|---|---|---|
| 132726 | 2/1985 | European Pat. Off. |
| 158464 | 10/1985 | European Pat. Off. |
| 190776 | 8/1986 | European Pat. Off. |
| 234867 | 9/1987 | European Pat. Off. |
| 3017246 | 11/1981 | Fed. Rep. of Germany |
| 53-26868 | 3/1978 | Japan |
| 8912587 | 12/1989 | PCT Int'l Appl. |
| 8912588 | 12/1989 | PCT Int'l Appl. |
| 8912589 | 12/1989 | PCT Int'l Appl. |
| 8912590 | 12/1989 | PCT Int'l Appl. |
| 9105714 | 5/1991 | PCT Int'l Appl. |
| 13504 | of 1911 | United Kingdom |
| 922317 | 3/1963 | United Kingdom |

OTHER PUBLICATIONS

L. M. Rogiers, ICI Specialty Chemicals, *New Formulation Trends in the Agricultural Industry*, Reprint #RP25/88E, pp. 3-11 (Nov. 1988).

B. F. Goodrich, *Carbopol® Water Soluble Resins*, p. 5 (Sep. 1987).

Ciba-Geigy agro (Product Advertisement), *Le Nouvel Agriculteur*, pp. 34, 35 (Feb. 22, 1991).

*Primary Examiner*—Jimmy G. Foster
*Attorney, Agent, or Firm*—Morgan & Finnegan

[57] ABSTRACT

A package containing a pesticidal composition which package comprises a first sheet of non-planar water soluble or water dispersible material defining a concavity enclosing the pesticidal composition, a second sheet of water soluble or water dispersible material sealed to the first sheet by a continuous closed water soluble or water dispersible heat seal, and a third sheet between the first and second sheets and sealed thereto by a water soluble or water dispersible seal to divide the package into two compartments. A process for making the package.

30 Claims, 1 Drawing Sheet

WATER SOLUBLE PACKAGE

This is a continuation of co-pending application Ser. No. 07/782,092, filed on Oct. 24, 1991, now abandoned, which is a continuation-in-part of U.S. Pat. application Ser. No. 07/713,684, filed Jun. 11, 1991, now abandoned, which is a continuation in part of U.S. patent application No. 07/680,301 filed Apr. 4, 1991, which is a continuation-in-part of U.S. patent application No. 07/679,290 filed Apr. 2, 1991, now abandoned, which is a continuation in part of U.S. patent application Ser. No. 07/554,615, filed Jul. 18, 1990, now U.S. Pat. No. 5,080,226, all of which are incorporated herein by reference.

BACKGROUND OF THE INVENTION

1. Field of the Invention

This invention relates to a water soluble or water dispersible package containing separate components of a final composition, and to a process for producing such a package.

2. Discussion of Background

Pesticides, e.g. herbicides, are often potentially harmful materials and are commonly produced as a concentrated solution or dispersion in an organic liquid, as a gel or in solid form. Such chemicals are typically supplied in a metal or blow-moulded plastics container. To use the chemical pesticides, e.g. herbicides, a quantity of the pesticide is measured out of the container in concentrated form and then mixed with a large volume of water before being sprayed onto a locus to be treated or onto plants. Such concentrated materials are frequently highly toxic so great care must be taken in measuring and mixing them to avoid spillage and to avoid human or animal contact with the concentrated pesticide. Efforts have been devoted to the design of containers to minimise the risk of accidental spillage of their contents when used and also to reduce residues remaining in the containers after use. Plastics containers with wide necks to facilitate pouring of their contents have been used. Blow-moulded plastics containers having hollow handles have been made in which the hollow handles are isolated from the body of the container to avoid retention of material in the handle.

Nevertheless, with present packages it is relatively easy to spill the contents during the mixing process with the resulting risk of contamination of the environment and risk of contact with humans or animals. Also, it is relatively rare to empty containers. Thus farmers, and other users, tend to have partly full containers left around. These represent a further hazard. Even when all of the contents have been used it is difficult to dispose of the empty container. It is also difficult to wash adequately the containers and measuring instruments in which the concentrated pesticides are handled. These devices represent a further hazard to personnel and to the environment.

It has been proposed to package agricultural chemicals in a container comprising a screw fitting adapted to screw onto a corresponding fitting on a spray tank. The contents of the container should be released only when a satisfactory seal exists between the tank and the container. Practical difficulties exist in securing widespread use of such a system in view of the need for standardisation of screw fitting sizes and the possibility of leakage if a satisfactory tight seal is not achieved.

It has also been proposed to package chemicals in a water soluble container which releases the packaged chemical only after contact with water. Such applications have however been limited by the capabilities of known water soluble containers which are often too prone to rupture. It has also proved difficult to avoid pinholes at heat-sealed joints in containers leading to leaking of the contents and unacceptable weakness in the material of the container adjacent to heat sealed joints.

SUMMARY OF THE INVENTION

The present invention seeks to overcome the disadvantages of known packages and to provide a package, and a method for producing the package, which contains a toxic, or most preferably pesticidal, composition and has one or more of the following advantageous features:

the packaged chemical is released only after contact with water in which it is to be dissolved or dispersed, minimising the possibility of accidental contact of the undiluted material with the environment or with humans or animals;

the chemical can be provided in unit dosage form suitable for dilution with a predetermined amount of water removing the need for undiluted chemical to be measured out;

the packaged chemical is easy to use: the packaged chemical can be simply placed in water prior to use of the chemicals;

the need for washing out of the residual chemical from containers to render them safe for disposal is removed: containers which have been in contact with the packaged chemical remain uncontaminated which facilitates their disposal; and the chemical is in two component form with the two separate components both stored so as to be released for mixture and contact with water when activation is required.

At least one of the packaged components is toxic. Typically the toxic component is an agrochemical, preferably a pesticidal composition or plant growth regulator, most preferably it is the pesticidal composition. For the purposes of the present specification and/or claims, the terms "toxic" and "agrochemical" encompass pesticidal compositions and plant growth regulators.

DETAILED DESCRIPTION OF THE INVENTION

Figure 1:
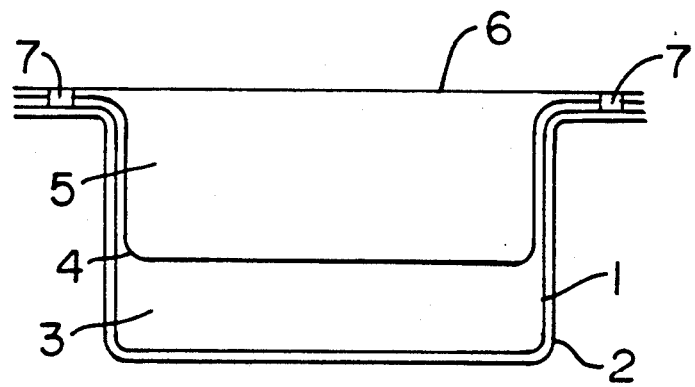
FIG. 1 illustrates a first embodiment of the present invention.

We have now devised a new package which dissolves in water, may be cheaply and easily produced and is unexpectedly strong and resistant to rupture or breakage.

Accordingly the present invention provides a package containing a pesticidal composition which package comprises a first sheet of non-planar water soluble or water dispersible material, a second sheet of water soluble or water dispersible material superposed on the first sheet and sealed to it by a continuous closed water soluble or water dispersible heat seal along a substantially planar continuous region of the superposed sheets, and a third sheet between the first and second sheets and joined to them along the continuous closed water soluble or water dispersible heat seal, whereby the third sheet divides the package into two sealed compartments which open on exposure of the package to water.

The invention further provides a process for producing a package which comprises; moulding a first sheet of water soluble or water dispersible material to form a non-planar sheet comprising at least one recess adapted to retain a pesticidal composition, the recess being bounded by a substantially planar flange;

placing at least one component of a multi-component composition in the at least one recess;

placing a second sheet on the flange and across every recess;

placing a third sheet of water soluble or water dispersible material over said second sheet to enclose therewith at least one further component of said multi-component composition; and heat sealing the first, second and third sheets along the flange to form a continuous water soluble or water dispersible heat seal.

The composition is preferably a pesticidal composition, more preferably in the form of two components which are to be stored apart and mixed only when the composition is to be activated for use.

The pesticidal composition may be in liquid form, or solid form, or gel form. It may comprise any conventional carrier or diluent or surfactant. Where the composition is in liquid form it may be in the form of a solution or of a dispersion in an organic liquid, e.g. an emulsion or a suspension. Similarly in gel form, the composition may contain pesticide either dissolved or dispersed in the substantially dry medium.

The packages of the present invention generally contain from 0.1 grams to 7 KG, preferably 1 g to 5 Kg, where the composition is in solid form. Where the composition is in liquid or gel form, the package typically contains from 1 ml to 10 liters, preferably from 0.5 to 5 liters.

Generally the package will contain at least a small amount of space, e.g. at least about 5% by volume, so as to minimise the likelihood of spillage of the composition during the production of the package.

Typically the two sheets of water soluble or water dispersible material are of the same material, but they may be different.

When the pesticidal composition is in liquid or gel form and comprises an organic solvent, the water soluble or water dispersible material will be one which is insoluble in the organic solvent.

Suitable water soluble or dispersible materials are polyethylene oxide and methyl cellulose. More preferably a polyvinyl alcohol (PVOH) film is used. Such a PVOH file may be a partially or fully alcoholised or hydrolysed, e.g. 40–99%, preferably 70–92% alcoholised or hydrolysed, polyvinyl acetate film.

The polyvinyl alcohol film may be unoriented, monoaxially oriented or bi-axially oriented. Water soluble materials are preferred since they provide less disposal problems. The materials used will generally be cold water soluble; cold water soluble polyvinyl alcohol is preferred. It will be understood that other materials may be used when the package is to be dissolved or dispersed in water or hot water. Generally the water soluble or water dispersible material will be flexible.

The maximum tensile strength of the material of the envelope is preferably at least 20, more preferably from 30 to 80, N/mm$^2$ and the elongation at break is preferably 200 to 380%, more preferably from 220 to 350%. Testing for these values is generally carried out at 23° C. and 50% relative humidity.

When the pesticidal composition is in liquid or gel form it is particularly important to avoid pinholes in the package through which leakage of the composition may occur. In such cases therefore the water soluble or water dispersible material will typically be a laminate, generally of two layers of different, or preferably the same, water soluble or water dispersible material, as pinholes are unlikely to coincide in two layers of material. Typically the laminates will consist of 2 layers of thickness from 20 $\mu$m to 1 mm, preferably about 40 $\mu$m, each. Generally however the thickness of the layers will be kept to the minimum needed to prevent rupture of the package, so that the water soluble or dispersible material is dissolved or dispersed as quickly as possible and the pesticide then released.

When the pesticidal composition is in solid form, the sheets of water soluble or water dispersible material typically comprise a single layer of material. In such case the material will generally be from 20 to 500 $\mu$m, preferably 30 to 100 $\mu$m, thick. However, in cases where it is particularly desirable to avoid pinholes in the package, e.g. to prevent the escape of unpleasant odours, a laminate material of the type described above may be used. As with packages containing liquids and gels, the thickness of the water soluble dispersible material will generally be kept to a minimum in packages containing solid compositions.

The two water soluble or water dispersible sheets in the packages are sealed together by a closed continuous heat seal. Typically to ensure that the seal is water soluble and does not suffer from leakage, it is a single continuous seal and has no geometrical discontinuities, i.e. it does not comprise any angular intersections with itself. Therefore the heat seal will usually be curved, at least in portions, for instance at the corners of the package.

Suitable pesticides which may be used in the package of the present invention include fungicides, insecticides and herbicides (for example hydroxybenzonitrile herbicides, e.g. bromoxynil or ioxynil or derivatives thereof such as salts or esters, e.g. heptanoates or octanoates). Molluscicides, suitable for addition to, for example, ponds or streams may also be employed.

Where the pesticidal composition is in liquid form, then suitable organic solvents which may be used as carriers in the pesticidal composition include petroleum based solvents, e.g. petroleum ethers, mineral oils, aliphatic or aromatic hydrocarbons, e.g. hexane, octane, cyclohexane, benzene, xylene and naphthalene, halogenated aliphatic or aromatic hydrocarbons, e.g. carbon tetrachloride, chloroform, methylene chloride and chlorobenzene, esters, e.g. amyl acetate, ketones, e.g. cyclohexanone, ethers, or a higher alcohol (lower alcohols may migrate through the water soluble or water dispersible materials described above: this can result in product appearing on the outside of the envelope). It will be understood that mixtures of solvents, e.g. mixtures of a hydrocarbon solvent with another solvent such as a ketone or a higher alcohol, may also be used. The organic liquid must be reasonably dry and typically contains less than 2 to 3% of water to ensure that it does not leak prematurely from the package.

Such compositions may comprise, in addition to, or in some cases instead of, an organic solvent as a carrier or diluent, a surfactant, which is reasonably dry in that it contains less than 2 to 3% water. Suitable surfactants may be of the ionic or non-ionic types: for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the pesticidal composition may comprise up to 10%, e.g. from 0.05% to 10% of surfactant but, if desired, it may comprise higher proportions of surfactant for example up to 15% in liquid emulsifiable suspension concentrates and up to 25% in water soluble concentrates.

The contents of the package may be thickened or rendered thixotropic to provide a gel. An increased viscosity in the contents can reduce the likelihood of rupture if the package is subjected to mechanical shock. The contents of the package may be rendered more viscous or thixotropic by the inclusion of additives, for example, a modified organophile, or bentonite, lecithin, polymethylene oxide or silica gel.

The concentrations of pesticide or herbicide dissolved or dispersed in the organic liquid or in the gel will generally be those conventionally used: in order to reduce the bulk of each package, however, concentrations may be increased. Each package will preferably contain at least about 500 ml and will preferably contain a convenient standard volume, for example 500 ml or 1 liter, although it will be appreciated that any convenient standard volume may be chosen.

When the pesticidal composition is in solid form then it may comprise any conventional carrier or diluent which is reasonably dry, in that it contains less than 2 to 3% of moisture. Examples of suitable solid diluents or carriers are aluminum silicate, talc, calcined magnesia, kieselguhr, tricalcium phosphate, powdered cork, adsorbent carbon black and clays such as kaolin and bentonite. Solid compositions may comprise surfactants, such as dispersing agents, for example those surfactants, previously mentioned. In some cases such surfactants may also be used as diluents or carriers.

As with compositions in liquid form, the concentration of pesticide in the solid pesticidal compositions may be as conventionally used: concentrations may however be increased to reduce the bulk of the package.

The pesticidal compositions used in the package of the present invention may be prepared by conventional means.

The packages of the present invention may be inside an additional outer container. Such a container may provide additional strength and if water resistant may serve to protect the package of the present invention from accidental exposure to water. The outer container is preferably sealed to avoid exposing the package of the present invention to undue moisture.

It will be appreciated that the package of the present invention comprises more than one compartment which may contain the same pesticidal compositions or components of a multi-component composition. Such multi-compartment packages are particularly useful where a combination of components are to be employed together and where the components are incompatible for a prolonged period, for instance if they react chemically.

Although it is preferred that the dividing sheet which separates the two compartments of the package itself be formed of water soluble or water dispersible material, any other material compatible (as regards heat sealing) with that used for each of the outer sheets can be used because removal of the two outer sheets by dispersion or dissolution will release the two components of the composition for dilution in the surrounding mass of water and for reaction when they come into contact with one another. The fact that the dividing sheet may still be present in the thus-constituted pesticidal composition will be no great disadvantage provided this does not lead to disturbance of mechanical handling operations such as spraying of the composition (for example by the sheet blocking the spray holes). Where the dividing sheet itself dissolves or disperses, the best possible results are obtained.

The structure of the package may in one example comprise a single thermoformed tray having a first component of the pesticidal composition placed on the floor of the tray and then covered by a dividing sheet which ultimately becomes sealed to the flanges of the thermoformed tray by sealing, and then the completion of the package would comprise placing a second component on the dividing sheet and subsequently covering that second component with a further water soluble or water dispersible sheet which thus encloses a second component and closes the package as a whole.

A further possibility involves the formation of two flanged trays, by thermoforming or vacuum forming, of water soluble or water dispersible sheet material and then filling the first tray with at least one first component, covering that tray with the dividing sheet and sealing the covering sheet to the flanges of the tray to enclose said at least one first component, then placing at least one further component in the second thermoformed tray and covering it with the already completed first thermoformed tray, its contents and dividing sheet whereby the cover sheet for the first tray then forms the dividing sheet between the first and second trays; the sealing of the package is completed by sealing the dividing sheet material which covers the flanges of the first tray to the flanges of the second tray, by a water soluble or water dispersible seal.

It is also envisaged that the package may comprise loosely formed pouches which include a third sheet in the structure to divide a first compartment from a second compartment, where the third sheet is optionally water soluble or water dispersible and is in any case sealed to the perimeters of the two outside sheets, with the various components of the herbicidal composition in the package to either side of the third sheet. Such a package may be formed by leaving the heat seal open along one edge of the package so as to allow access of a filling nozzle into the package alternately to each side of the dividing sheet, and then completing the seal to close the two compartments and to form a continuous water soluble seal around the dividing sheet. The degree of filling of the pouches will maintain two limp water soluble or water dispersible outer sheets in a non-planar configuration.

If desired, there may be several such containers joined edge-to-edge, for example by using a thermoformed tray which has a plurality of compartments therein separated by web regions of the dividing sheet.

It will be appreciated that a multi-component pesticidal composition may be stored in more than two compartments if additional dividing sheets are provided, with a component of the composition sandwiched between two of the dividing sheets of such a package.

Although the above description is limited to the use of a herbicidal composition, it is envisaged that the water soluble package in accordance with the present invention may be used for other multi-component materials which are hazardous, i.e. toxic, upon exposure of humans thereto but which are desired to be combined in a safe environment, for example in a water tank.

Preferably the packages according to the invention should release their contents in less than about 10 minutes. Typically the packages will be placed in the spray tank of a conventional sprayer. The tank will generally be partly filled with water, and the package added. When the tank is provided with means to agitate the water, the contents of the bag will be released more rapidly. It is preferred that release should take place in less than a minute, for example in 30 to 40 seconds. It will be understood that the time taken to release the pesticide will depend upon a number of factors apart from the nature of the bag, including the temperature of the water and the level of agitation.

The packages of the present invention may be obtained by first deforming a sheet of water soluble or dispersible material so as to form a recess adapted to retain a pesticidal composition. This may be achieved for example by a vacuum forming where the sheet is deformed to conform to the shape of a suitable mould and may, if desired, be a thermoforming process to cause the sheet to retain its shape after release from the mould.

Where the deformation is by vacuum forming, the mould may be equipped with pinholes through which the space between the mould and the sheet can be evacuated.

Where deformation is by thermoforming, the sheet may be driven against the mould by vacuum forming, or by applying a superatmospheric pressure to the other side of the sheet, or by mechanical displacement of the sheet (plug forming).

Packages according to the invention are shown, by way of illustration, in the accompanying drawings in which:

FIG. 1 illustrates a package formed by thermoforming or vacuum forming a sheet (1) of water soluble material into a mould (2), a first component (3) of a pesticidal composition being placed in the recess formed and covered by a second sheet (4) of water soluble material. A second component (5) of a pesticidal composition is contained in a recess above the second sheet (4) and a third sheet (6) of water soluble material covers the second component of the pesticidal composition. A heat seal (7) on the flange of the package then provides the necessary seal.

Figure 2:
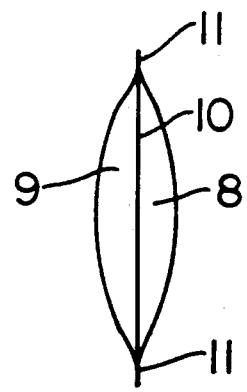
FIG. 2 illustrates a second embodiment of the present invention.

FIG. 2 illustrates a package in which a first component (8) and second component (9) of a pesticidal composition are contained in a package which comprises two loosely formed pouches and a third sheet (10) which is optionally water soluble or water dispersible and is heat sealed (11) to the perimeters of the two outside sheets.

It will be understood that, for example, two adjacent sheets (1) and (4) or sheets (1) and (6) or (4) and (6) may be derived from a single sheet of material by folding.

In order to ensure optimum processability the heat sealing is generally carried out at 15° to 25° C. and 15 to 85% relative humidity (RH). The relative humidity is preferably 35 to 55%. Some routine experimentation may be required to obtain a suitable heat seal depending on the package material, e.g., the particular grade and thickness of PVOH chosen. The quality of the seal can be checked, for example by visual inspection for areas of capacity or for bubbles. Imperfections in the seal may give rise to a lack of water solubility or water dispersibility of the seal. The heat sealing process can be carried out on conventional heat sealing equipment which permits control variation of the sealing jaw temperature, jaw pressure and dwell time.

While specific embodiments of the present invention have been shown and described, it should be apparent that many modifications can be made thereto without departing from the spirit and scope of the invention. Accordingly, the invention is not limited by the foregoing description, but is only limited by the scope of the claims appended thereto.

We claim

1. A package for containing at least one toxic composition which package comprises a first sheet of non-planar water soluble or water dispersible material, a second sheet of water soluble or water dispersible material superposed on the first sheet and sealed to it by a continuous closed water soluble, or water dispersible heat seal along a substantially planar continuous region of the superposed sheets, and a third sheet between said first and second sheets and joined to them along said continuous closed water soluble or water dispersible heat seal, whereby said third sheet divides said package into first and second sealed compartments which open on exposure of the package to water.

2. A package according to claim 1, in which the third sheet is water soluble.

3. A package according to claim 1, wherein the first, second and third sheets are made of the same material.

4. A package according to claim 1, in which the said water soluble or water dispersible sheets each comprise a laminate of at least two layers of water soluble or water dispersible material.

5. A package according to claim 4, which comprises two layers each having a thickness from 20 $\mu$m to 1 mm.

6. A package according to claim 1, in which the toxic composition is an agrochemical.

7. A package according to claim 6, in which the toxic composition is a plant growth regulator.

8. A package according to claim 6, in which the toxic composition is a pesticidal composition.

9. A package according to claim 8, each compartment containing a composition, at least one of the said contained compositions being said pesticidal composition.

10. A package according to claim 8, in which the pesticidal composition is in liquid or gel form.

11. A package according to claim 8, containing a pesticidal composition in solid form in which each of the first, second and third sheets comprises a single layer of water soluble or water dispersible material.

12. A package according to claim 11, in which each sheet has a thickness from 20 to 500 $\mu$m.

13. A package according to claim 8, which contains from 1 ml to 10 liters of pesticidal composition in liquid or gel form or from 0.1 grams to 7 Kg of pesticidal composition in solid form.

14. A package according to claim 1, in which the first sheet has a recess and the first compartment is defined by this recess.

15. A package according to claim 1, in which the heat seal is a single continuous seal not comprising any intersections with itself.

16. A package according to claim 1, in which the water soluble or water dispersible material comprises polyethylene oxide, methyl cellulose or a polyvinyl alcohol.

17. A package according to claim 16, in which the water soluble or water dispersible material comprises a cold water soluble polyvinyl alcohol which is 40 to 99% hydrolysed or alcoholised polyvinyl acetate.

18. A package according to claim 1, in which the contents are releasable in less than 10 minutes after contact with water.

19. A package according to claim 18, in which the contents are releasable in less than 1 minute.

20. A package according to claim 19, in which the hydroxybenzonitrile herbicide comprises a mixture of ioxynil and bromooxynil esters.

21. A package according to claim 1, in which the toxic composition comprises a hydroxybenzonitrile herbicide.

22. A package according to claim 1, in which said first compartment contains a first pesticidal composition and said second compartment contains a second pesticidal composition.

23. A process for producing a package according to claim 1 which comprises the steps of:
moulding a first sheet of water soluble or water dispersible material to form a non-planar sheet comprising at least one recess adapted to retain a pesticidal composition, said recess being bounded by a substantially planar flange;
placing at least one component of a multi-component composition in said at least one recess;
placing a second sheet on the flange and across every said recess;
placing a third sheet of water soluble or water dispersible material over said second sheet to enclose therewith at least one further component of said multi-component composition; and
heat sealing the first, second and third sheets along the flange to form a continuous water soluble or water dispersible heat seal.

24. A process according to claim 23, in which the first water soluble or water dispersible sheet is deformed by vacuum-forming to conform to a mould.

25. A process according to claim 24, in which the first, second and third sheets are heat sealed at a sealing temperature of from 140° to 220° C.

26. A process according to claim 24, in which the first, second and third sheets are heat sealed at a sealing jaw pressure from $1 \times 10^{-4}$ to $3.5 \times 10^{-4}$ kg/m$^2$.

27. A process according to claim 24, in which the first, second and third sheets are heat sealed with a dwell time from 0.2 to 1.5 seconds.

28. A process according to claim 24, in which the sheets are heat sealed at a relative humidity of from 15 to 85%.

29. A process according to claim 23, wherein said third sheet is also deformed to be non-planar.

30. A process according to claim 23, wherein each said deformed sheet is deformed by thermoforming.

* * * * *